(12) United States Patent
Mansouri

(10) Patent No.: US 7,717,879 B2
(45) Date of Patent: May 18, 2010

(54) ANESTHETIC SYRINGE

(75) Inventor: Said Mansouri, Aachen (DE)

(73) Assignee: SMJM Inject GmbH, Aachen (DE)

( * ) Notice: Subject to any disclaimer, the term of this patent is extended or adjusted under 35 U.S.C. 154(b) by 0 days.

(21) Appl. No.: 10/533,709

(22) PCT Filed: Feb. 3, 2005

(86) PCT No.: PCT/DE2005/000178

§ 371 (c)(1),
(2), (4) Date: May 3, 2005

(87) PCT Pub. No.: WO2005/075009

PCT Pub. Date: Aug. 18, 2005

(65) Prior Publication Data

US 2006/0052753 A1    Mar. 9, 2006

Related U.S. Application Data

(60) Provisional application No. 60/541,811, filed on Feb. 4, 2004.

(30) Foreign Application Priority Data

Feb. 3, 2004   (DE) .................. 10 2004 005 383
May 7, 2004   (DE) .................. 10 2004 023 235

(51) Int. Cl.
*A61M 5/00*    (2006.01)

(52) U.S. Cl. .............. 604/187; 604/140; 604/141; 604/218

(58) Field of Classification Search .............. 604/68, 604/70, 131, 140, 141, 143, 147, 187, 218
See application file for complete search history.

(56) References Cited

U.S. PATENT DOCUMENTS 2,650,591 A    9/1953   Love (Continued)

FOREIGN PATENT DOCUMENTS

DE    25 00 851    6/1976

(Continued)

OTHER PUBLICATIONS

Written Opinion of the International Searching Authority in PCT/DE2005/000178 dated Oct. 12, 2006.

*Primary Examiner*—Kevin C Sirmons
*Assistant Examiner*—Bhisma Mehta
(74) *Attorney, Agent, or Firm*—Collard & Roe, P.C.

(57) ABSTRACT

An improved, very wieldy anesthetic syringe that allows for precise and repeated injection has a first hydraulic chamber behind a feed piston and a second hydraulic chamber behind the first hydraulic chamber, the hydraulic chambers being connected so as to allow for regulation of the flow resistance. A special receiver for cannulae that have been specifically developed for use with the proposed syringe is also provided.

13 Claims, 2 Drawing Sheets

U.S. PATENT DOCUMENTS

| | | |
|---|---|---|
| 4,006,736 A | 2/1977 | Kranys et al. |
| 4,710,172 A | 12/1987 | Jacklich et al. |
| 5,180,371 A | 1/1993 | Spinello |
| 5,690,618 A | 11/1997 | Smith et al. |
| 5,730,723 A * | 3/1998 | Castellano et al. ............ 604/68 |
| 6,440,099 B2 * | 8/2002 | Haar et al. .................... 604/68 |
| 2002/0055712 A1 * | 5/2002 | Neracher .................... 604/143 |
| 2003/0105433 A1 | 6/2003 | Ruben |
| 2003/0195477 A1 | 10/2003 | Ruben |
| 2004/0055662 A1 * | 3/2004 | Neracher ..................... 141/27 |

FOREIGN PATENT DOCUMENTS

| | | |
|---|---|---|
| DE | 196 14 337 | 8/1997 |
| DE | 196 43 813 | 4/1998 |
| DE | 19643813 | 4/1998 |
| EP | 0 567 186 | 4/1993 |
| WO | WO 01/13973 | 3/2001 |
| WO | WO 02/49697 | 6/2002 |
| WO | WO 02/081009 | 10/2002 |
| WO | WO 03/041765 | 5/2003 |

* cited by examiner

ANESTHETIC SYRINGE

CROSS REFERENCE TO RELATED APPLICATIONS

Applicant claims priority under 35 U.S.C. §119 of German Application No. 10 2004 023 235.0 filed May 7, 2004; German Application No. 10 2004 005 383.9 filed Feb. 3, 2004; and U.S. Provisional Application No. 60/541,811 filed Feb. 4, 2004. Applicant also claims priority under 35 U.S.C. §365 of PCT/DE2005/000178 filed Feb. 3, 2005. The international application under PCT article 21(2) was not published in English.

The invention relates to an anesthetic syringe.

In many medical fields, the medical staff is regularly confronted with the task of injecting an anesthetic into the human or animal body. Anesthetic syringes, which have substantially proved efficient, are used for this purpose.

A great majority of the anesthetic syringes used in practice are for manual operation. This kind of anesthetic syringes is so well known that it needs no further explanation.

To improve control and repeatability of the injection process using an anesthetic syringe, fully automatic and semiautomatic anesthetic syringes have also been suggested. The document DE 196 43 813 A1 for example discloses a kit for a syringe provided with a control electronics unit suited for calculating the drug flow. A photooptical readout system provides feedback as to the forward progress of the piston.

The German patent application published for opposition 25 00 851 shows an injector of contrast medium, said injector controlling the through-flow, the total injection amount and the pressure of the contrast medium via a control electronics unit.

The document WO 01/13973 A2 shows a similar device where the control unit is substantially separated from the injection syringe and injection pressure is controlled with a foot pedal.

These systems however are all very complicated and unwieldy. The document EP 0 567 186 B1 proposes an improvement in the form of a hand-held syringe driver in which a piston is pushed through a carpule volume by a motor-driven threaded rod. For driving the motor, it suffices to connect an electric cable to the power supply.

U.S. Pat. No. 5,180,371 proposes an anesthetic syringe where an external control unit alternately fills and empties two chambers in the syringe via a hydraulic line. The chambers are respectively located on the front side and on the rear side of a piston plate through which a feed piston connected to the piston plate is advanced through a carpule volume and pushes the content of the carpule through a needle for injection. As a result, the anesthetic is expelled in a particularly controlled manner, which is said to reduce the required total amount of anesthetic.

U.S. Pat. No. 5,690,618 pursues the same objective in proposing an electronic anesthetic syringe where an electronic drive with an external power source is disposed in a syringe housing of a pen-style arrangement, thus allowing for better handling of the syringe.

To the present, the leading developed implementation is considered tobe the one disclosed in WO 03/041 765 A1. The anesthetic syringe suggested therein is also configured substantially like a pen and is easy to operate as a result thereof. However, it functions on its own, that is, independently of an external power source. For this purpose, a gas cartridge is screwed to the syringe, said cartridge generating in a rear hydraulic chamber a drive pressure via a pleated bellows connected to the cartridge. After a closure in a hydraulic channel has been opened, said pressure also prevails in a front hydraulic chamber surrounding a feed piston. A resulting forward driving force is generated on a piston plate in accordance with the size of the piston rod. As a result thereof, the piston is pushed through a carpule volume and an anesthetic is expelled from the syringe. When the hydraulic channel is closed, the front hydraulic chamber prevents the piston from being pulled out of the syringe.

This anesthetic syringe is quite complicated to manufacture, though. It more specifically needs a plurality of expensive seals and a hydraulic channel, which is difficult to form, for connecting the two hydraulic chambers located in front and behind the piston plate.

It is the object of the present invention to provide an improved syringe that is independent of external power sources.

The solution to this object is an anesthetic syringe with a feed piston that is longitudinally slidable in a carpule volume and is connected at a pressure plate to a first hydraulic chamber, a second hydraulic chamber being provided in the syringe behind the first hydraulic chamber, said second hydraulic chamber being connected to the first hydraulic chamber so as to allow for regulation of the flow resistance.

Arrangement of the second hydraulic chamber "behind" the first hydraulic chamber means that the second hydraulic chamber is not disposed on the feed piston—and in front of the piston plate as viewed in the feed direction—but that it is rather connected in series to the first hydraulic chamber by which it is separated from the feed piston. Accordingly, one aspect of the invention is embodied by rearranging the hydraulic system (which includes at least the first hydraulic chamber) for providing forward driving force and for controlling the forward drive. Advantageously, a much greater pressure is thus available for driving the feed piston forward. Tests have shown that the hydraulic chamber for driving the feed piston must exert pressures of up to 150 bars so that the anesthetic syringe can be used in a wide variety of applications. If the hydraulic chambers are arranged as suggested, no back pressure is generated at the pressure plate of the feed piston so that the entire pressure of the first hydraulic chamber can be used for the resulting feed force of the feed piston. The syringe may further be implemented with a slimmer structure because there is no longer a need for a hydraulic line beside the piston plate.

It should be emphasized that this advantage can also be ensured if the two hydraulic chambers are arranged side by side in the syringe, with the two however being disposed behind the feed piston. Such an arrangement is also advantageous and inventive independent of all of the other features of the present invention.

In a preferred embodiment of the syringe of the invention a separator piston is located behind the second hydraulic chamber, said separator piston being slidably mounted so as to be capable of reducing the size of the second hydraulic chamber. Meaning, the second hydraulic chamber can be reduced in size by accordingly displacing the separator piston.

A separator piston permits to generate a driving pressure in the second hydraulic chamber in a simple and at the same time variable manner. The separator piston may for example be mounted in the anesthetic syringe via a strong spring that permanently exerts a pressure onto the second hydraulic chamber.

However, it is more specifically proposed that the separator piston projects into a pressurization space and is slidably mounted so as to be capable of enlarging the same, displacement of said separator piston so as to enlarge the pressurization space effecting a reduction in the size of the second hydraulic chamber. This makes it possible to operate the hydraulic system separately from an additional pressurization space; said pressurization space may thereby be filled with a liquid or a gas. The pressurization space is particularly easy to implement if a gas is to be stored therein. As compared to liquids, gases are much easier to compress. Accordingly, a pressurized gas contained in the pressurization space can act through the separator piston onto the hydraulic system, more specifically onto the second hydraulic chamber. Accordingly, the pressurization space can be used as a gas spring.

The separator piston is preferably mounted so as to be slidable backward (so as to reduce the pressurization space while enlarging the size of the second hydraulic chamber). In this form, the syringe can be used several times with the force of the spring being made use of repeatedly within the pressurization space.

It is advantageous if enlarging the pressurization space by displacing the separator piston causes the second hydraulic chamber to become smaller by the same amount. If the compressed gas is sufficiently prepressurized in the pressurization space, it is capable of pushing the separator piston quite far outward without causing the pressure in the pressurized chamber to drop too much. Under the suggested displacement conditions, that is, with a hydraulic ratio of 1:1, the separator piston can be ofa particularly simple implementation. A simple disk that concurrently bounds the pressurization space and the second hydraulic chamber and that is free to slide therebetween is particularly suited. A double seal can be provided at the rim of the disks for reliably separating the hydraulic system from the pneumatic system.

In order to be capable of filling the pressurization space with gas under overpressure conditions, it is suggested that the pressurization space comprises a fitting for a compressed gas supply, more specifically a receiving means for a gas cartridge.

In a particularly preferred embodiment, the anesthetic syringe of the invention comprises a slide valve capable of closing or progressively opening a control hole between the first hydraulic chamber and the second hydraulic chamber. The connection between the first and the second hydraulic chamber is particularly suited for fine regulation of the movement resulting at the feed piston when the second hydraulic chamber is subjected to high overpressure. This occurs particularly efficiently using a slide valve preferably having a substantially linear closure characteristic.

In order to allow for haptic feedback of the pressure that builds up as a result of the slide valve opening in the first hydraulic chamber, it is suggested that the slide valve has a pressure plate that is connected to the first hydraulic chamber. More specifically, a front element of the slide valve is capable of protruding into the first hydraulic chamber.

The major property of a slide valve is that it is capable of sliding along an axis of movement, a valve passage in the control hole being opened more or less depending on the position of the valve along the axis of movement. As soon as the slide valve is connected to the first pressurized chamber, or projects thereinto with but a part thereof, a hydrostatic force that pushes the slide valve along its axis of movement out of the first hydraulic chamber is generated when a pressure builds up in the first hydraulic chamber. Accordingly, the force with which the slide valve is pushed out of the hydraulic chamber is indicative of the pressure in the first hydraulic chamber. If the anesthetic syringe has a key switch with a touch-sensitive surface that causes the control hole to open (at least substantially) parallel to the axis of movement of the slide valve when pressed, the counterforce acting against the pressure exerted onto the touch-sensitive surface immediately haptically indicates the pressure in the first hydraulic chamber.

The syringe provides a particular good grip while allowing for simultaneous actuation of a key switch if the touch-sensitive surface thereof is at least partially disposed in a front half of the anesthetic syringe. In accordance with one aspect of the invention, the proposed anesthetic syringe is extremely wieldy. This can also be achieved by configuring the syringe (like a pen) so that the grip is very near to the tip and that it can be operated there. This permits the physician to guide the needlequite directly with part of the syringe projecting backward from his hand and not interfering with the placement of the injection. This can be particularly advantageous if the physician has to overcome increased resistance when placing the needle and if the syringe has to be pushed forward using accordingly high forces.

In order for the injection pressure to become noticeable independent of the force exerted along the longitudinal direction of the syringe it is proposed that an axis of movement of the slide valve be disposed at least substantially perpendicular to a longitudinal direction of the syringe. If the syringe has a substantially round shape, the slide valve can more specifically be disposed radially.

To ascertain that, independent of the hydraulic pressure in the first hydraulic chamber, the syringe will not effect any forward progress until it is intentionally actuated, it is proposed that the slide valve be biased with a biasing force that closes the control hole. For this purpose, a conventional spiral spring can be connected to the slide valve.

In an advantageous implementation variant of the anesthetic syringe of the invention, the latter has an indexer piston that is connected to the first hydraulic chamber. An indexer piston permits, as an alternative or in addition to haptic feedback, to also visually indicate the pressure in the first hydraulic chamber. For this purpose, the indexer piston can project into the first hydraulic chamber, more specifically with one foot, so that, if pressure builds up in the first hydraulic chamber, a resulting force acts onto the indexer piston, said force driving said piston out of the first hydraulic chamber. If the indexer piston is slidably mounted so as to protrude at least partially from the housing of the syringe, with a limit stop for limiting the exit thereof being preferably provided, it is possible to immediately identify the inside pressure by the extent the indexer piston has been pushed out of the housing of the anesthetic syringe. In order for the pressure in the first hydraulic chamber to be also readable in terms of measurement it is suggested that the indexer piston be mounted so as to be biased against the exit direction, with a bias provided by a conventional spiral spring being particularly suited since the displacement path of the indexer piston and the pressure applied for this purpose are proportionally coupled through the spring constant.

It is suggested that the syringe comprises a special receiving means for a special cannula so that only specific cannulae intended for use with the syringe of the invention can be used with the syringe. Said receiving means may for instance be a special thread, a special bayonet socket or a special detent means which receives the special cannula in such a manner that it is in fluid conducting communication with the glass carpule.

To ascertain that the feed piston will not be incidentally pulled out of the syringe housing (by drawing a negative pressure) it is proposed that the feed piston be completely received in a feed cylinder when in its inner position. As a result, when the pressure piston is drawn back into the anesthetic syringe, the cylinder wall is allowed to cover the tip of the feed piston so that the latter can no longer be grasped. The fitting for the carpule volume can be disposed at the cylinder wall projecting at the front.

It should be noted that an anesthetic syringe having a separator piston located in a pressurization space and in a second hydraulic chamber so as to be slidable and to thereby alternately vary the volume of both space and chamber is advantageous and inventive by itself. The same applies to an anesthetic syringe in which displacement of the separator piston additionally causes the volume of the pressurization space to vary by the same amount than the hydraulic chamber. This may be particularly readily achieved by a separator piston that has the same diameter in the pressurization space and in the second hydraulic chamber.

It should also be noted that an anesthetic syringe with a hydraulic or a pneumo-hydraulic drive that is designed to have a slide valve for haptic feedback is also advantageous and inventive independent of the other features. The same also applies for an anesthetic syringe having an indexer piston connected to the first or to the second hydraulic chamber.

The invention will be explained in closer detail with reference to the drawings showing an exemplary embodiment thereof. In the drawings.

Figure 1:
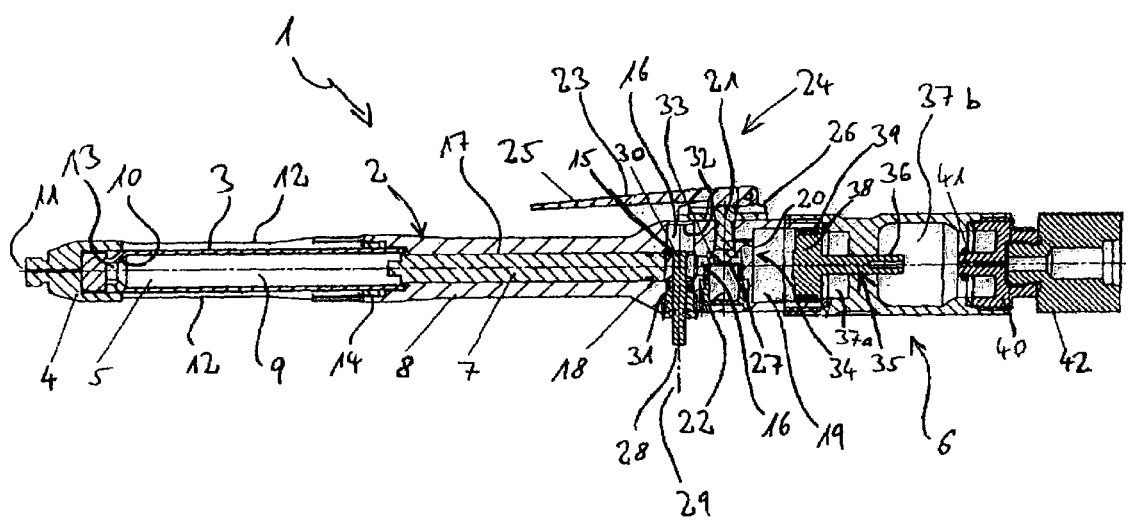
FIG. 1 shows an anesthetic syringe with carpule volume, feed piston, first hydraulic chamber, second hydraulic chamber, separator piston and pressurization space being connected in series.
Figure 2:
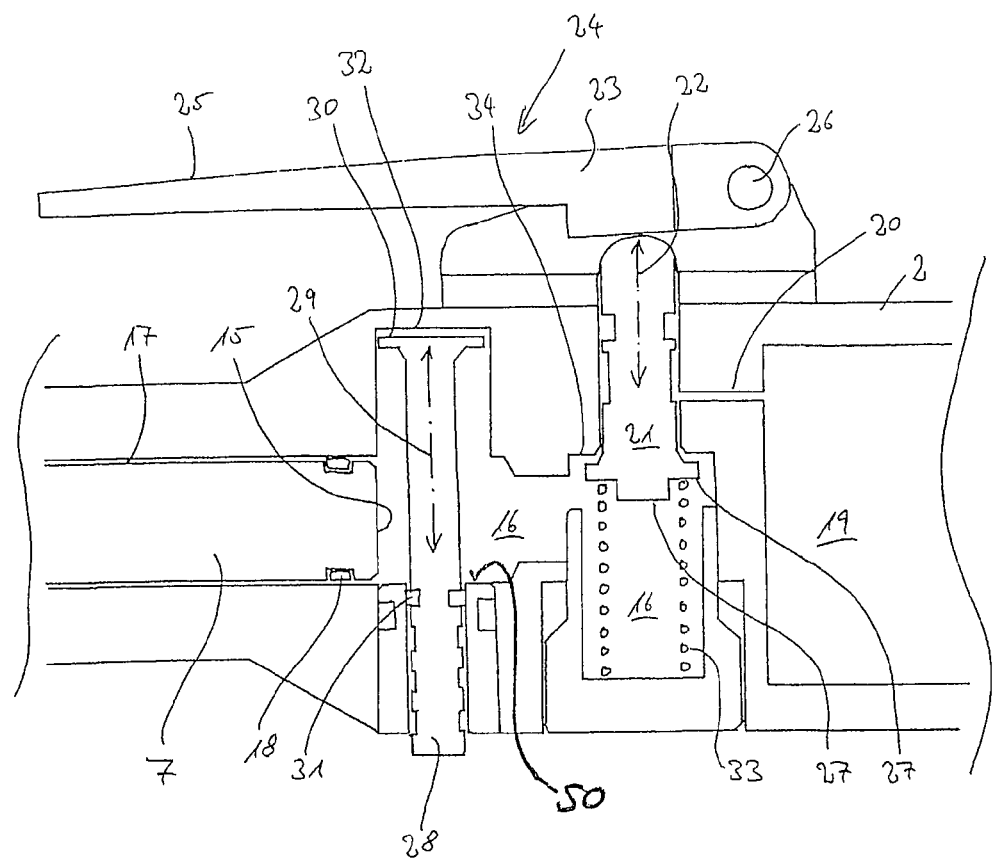
FIG. 2 shows the compression spring and the compression plate of the embodiment of FIG. 1 in detail.

The anesthetic syringe 1 of the unique figure substantially consists of a housing 2 capable of receiving a carpule 5 in a carpule volume 3 of a carpule case 4 and of expelling via a feed piston 7 the content thereof by means of a hydraulic-pneumatic drive system 6.

The feed piston 7 is mounted in a feed cylinder 8 so as to be slidable along the main axis 9 along which the anesthetic syringe 1 extends, said feed piston 7 adopting in the unique figure an inner end position and being adapted to be moved as far as an abutment shoulder 10 where it adopts an outer end position when it is being advanced along the axis 9. As the feed piston 7 progresses forward, it is moved through the carpule volume 3 so that liquid contained in an inserted carpule 5 can be expelled through a needle aperture 11 and injected. For use of the syringe 1, a cannula is inserted into the needle aperture 11. The cannula has a tip for piercing the tissue and a second tip for insertion into the sealing membrane of the inserted carpule 5.

A special receiving means for receiving the cannula (not shown in detail) is provided for in the needle aperture 11 to secure a cannula against unintentional insertion into the syringe 1, which mechanically fails under the sometimes prevailing high pressures.

The carpule case 4 has two inspection windows 12 through which the position of the advancing feed piston 7 within the carpule case 4 can be viewed. The carpule 5 has a head 13 with a design usual in commerce so that the treating physician is free to choose the carpule he already knows from working with conventional syringes. The carpule case 4 is firmly connected to the feed cylinder 8 through a bayonet socket 14.

With a pressure plate 15, the feed piston 7 faces a first hydraulic chamber 16, a surface area 17 of the feed piston 7 being sealed against the first hydraulic chamber 16 by an O-ring 18.

Behind the first hydraulic chamber 16 there is provided a second hydraulic chamber 19 that is connected to the first hydraulic chamber 16 by a control hole 20. The opening of the control hole 20 between the first hydraulic chamber 16 and the second hydraulic chamber 19 is regulated by a slide valve 21 that is mounted so as to be slidable along a direction of movement 22 and that abuts at an outer side of the housing 2 on a key switch arm 23 of a control key switch 24. Control key switch 24 comprises a touch sensitive surface 25 that is turned toward the front region of the syringe 1 and serves to push the key switch arm 23, and as a result thereof the slide valve 21, down. For this purpose, the key switch arm 23 is mounted on a key switch bearing 26 so as to be rotatable about a key switch bolt. The key switch bolt is perpendicular to the main axis 9 along which the anesthetic syringe 1 extends.

The slide valve 21 has a pressure plate 27 that projects into the first hydraulic chamber whereas the surface area of the slide valve 21 is sealed by an O-ring.

In similar fashion, an indexer piston 28 is mounted in the housing 2 along a direction 29 that is oriented radially with reference to the main direction 9 in which the syringe 1 extends. The indexer piston 28 may be slidably mounted so as to protrude at least partially from the housing 2 with a limit stop 50 being provided for limiting the exit thereof. With one foot 30, the indexer piston 28 projects into the first hydraulic chamber 16, whereas the surface area of the indexer piston 28 is sealed by an O-ring 31. A pressure spring (not shown) urges the indexer piston 28 towards an inner end position in which the foot 30 is brought to fit on an inner stop face 32 (for increased clarity, the indexer piston 28 is shown in its extended position against an abutment; in practice however, when the hydraulic chamber 16 is not pressurized, the indexer piston of the present implementation 1 adopts the inner end position).

An additional compression spring 33 urges the slide valve 21, which is biased to a rest condition, in the outer end position shown which is defined by abutment of the pressure plate 27 on the housing 2 against an abutment 34, said pressure plate being configured to be larger than the cylindrical portion of the slide valve 21.

The second hydraulic chamber 19 is bounded on its rear side by a separator piston 35 that is mounted so as to be slidable along the main direction 9 in which the syringe 1 extends and that in turn projects on the rear side into a pressurization space 37a, 73b, thus bounding the same. A pressure plate 38 constitutes the most important element of the separator piston 35. A double O-ring seal 39 is provided on sides of the pressure plate 38. In order to prevent the separator piston 35 from becoming wedged as it is being moved between the second hydraulic chamber 19 and the pressurization space, there is provided in the pressurization space 37a, 37b a guide means for a cylindrical guide rod 36 of the separator piston 35. Large passageways connect the two chamber portions 37a and 37b of the pressurization space (not shown in the figure).

On its rear side, the pressurization space 37b is bounded by a closure plug 40 that is sealingly connected to the pressurization space 37 by another O-ring 41 and that is provided with a check valve (not shown in detail) through which a gas cartridge or an adapter 42 for connecting a compressed gas line is connected to the syringe 1.

In operation, the hydraulic pressure needed to advance the feed piston 7 is generated by the pressurization space 37a, 37b. The separator piston 35 thereby separates the gas volume (which has been filled under pressure through the adapter 42 into the pressurization space 37a, 37b) from the hydraulic oil in the second hydraulic chamber 19. Through control hole 20, the pressurized hydraulic oil can flow to the slide valve 21. In its condition at rest, the slide valve 21 is closed by the compression spring 33. The compression spring is biased through a threaded lid (not labeled, disposed in the housing 2, on the side opposite the slide valve 21) in order to generate at the control hole 20 the sealing force needed. The valve is a two-way globe valve with a proportional characteristic so that the volume flow and, as a result thereof, the exiting speed of the feed piston 7 can be controlled as a function of the valve travel.

To extend the feed piston 7, the key switch arm 23 must be actuated, preferably at the touch-sensitive surface 25 thereof, toward the housing 2 of the syringe 1. As a result, the slide valve 21 is forcibly displaced against the compression spring 33 along its direction of movement 22 into the housing 2 of the syringe 1. The hydraulic oil is now allowed to flow from the second hydraulic chamber 19 to the first hydraulic chamber 16 through the flow cross-section which has thus come free. As a result, the pressure plate 15 of the feed piston 7 is put under pressure so that the feed piston 7 extends.

If a counterforce is applied to the feed piston 7 above the tissue into which the syringe 1 has been inserted, the pressure rises in the two hydraulic chambers as a result of the hydraulic losses at the control hole 20, the pressure rise being greater in the first hydraulic chamber 16, though. This pressure acts onto the foot 27 of the slide valve 21 in the closing direction of the valve. Through the key switch 24, the treating physician feels the change in pressure and must exert onto the key switch 24 an accordingly increased pressure in order for the slide valve 21 to remain in the opened position and for the valve of the control hole 20 to remain open.

In addition to this pressure sensing, a visual pressure display that indicates the cylinder pressure and, as a result thereof, the force of the piston, which can dictate the amount of pressure needed for injection, is provided by the indexer piston 28. The indexer piston 28 thereby acts as a small hydraulic cylinder that is simple to operate and at the piston of which there are formed three grooves for indicating the intensity of the pressure. In its condition at rest, the piston 28 is held in the housing 2 by the spring (this condition is not shown herein). As the hydraulic pressure in the first hydraulic chamber increases, a force is generated above the foot 30 of the indexer piston 28, said force counteracting the biasing force of the spring and causing the indexer piston 28 to extend, to a greater or lesser extent according to the hydraulic pressure conditions in the first hydraulic chamber 16, out of the housing 2 of the syringe 1 along the direction of movement 29. The pressure can be read by the grooves on the piston 28.

If the feed piston 7 is completely extended and the glass carpule 5 is empty as a result thereof, a new glass carpule must be inserted into the carpule case 4 for the next treatment. For this purpose, the carpule case 4 is detached from the housing 2 of the syringe 1 via the bayonet socket, the carpule is replaced and then the carpule case 4 is again connected to the feed cylinder 8 through the bayonet socket.

Additionally, the feed piston 7 must be returned to its inner end position. For this purpose, the syringe 1 must be placed into a charging station and the feed piston 7 pushed back through a lever mechanism. For this purpose, the charging station actuates the key switch arm 23 and opens the valve of the control hole 20 so that communication is established between the first 16 and the second hydraulic chamber 19. As the feed piston 7 is being pushed back, the separator piston 35 returns to the inner end position and causes the gas volume in the pressurization space 37a, 37b to be pressurized to the initial pressure.

To refill the syringe with the spring gas, which may be necessary after multiple use, or also to fill the syringe in the first place, the unique figure reveals a filling adapter 42. It serves to fill under pressure the pressurization space 37a, 37b with nitrogen. The check valve at the O-ring 41 prevents the gas from escaping when the adapter is unscrewed.

The invention claimed is:

1. An anesthetic syringe comprising:
(a) a slide valve comprising a front element;
(b) a feed piston longitudinally slidable within a carpule volume, said feed piston having a feed piston pressure plate;
(c) a first hydraulic chamber connected to said feed piston pressure plate;
(d) a second hydraulic chamber behind said first hydraulic chamber and connected to said first hydraulic chamber so as to allow for regulation of flow resistance;
(e) a control hole having an opening between said first hydraulic chamber and said second hydraulic chamber;
(f) a spring connected to said slide valve, said spring biasing said slide valve to a rest condition wherein the opening of the control hole between said first hydraulic chamber and said second hydraulic chamber is closed; and
(g) a separator piston that is disposed behind the second hydraulic chamber and that is slidably mounted so as to be capable of reducing the size of the second hydraulic chamber;
wherein said slide valve has a slide valve pressure plate connected to said first hydraulic chamber;
wherein said front element protrudes into said first hydraulic chamber in order to allow for haptic feedback of pressure in said first hydraulic chamber; and
wherein said slide valve is capable of closing or progressively opening the opening of the control hole between said first hydraulic chamber and said second hydraulic chamber.

2. The anesthetic syringe as set forth in claim 1, wherein the separator piston is slidably mounted so as to be capable of enlarging a pressurization space, displacement of said separator piston so as to enlarge the pressurization space effecting a reduction in the size of the second hydraulic chamber.

3. The anesthetic syringe as set forth in claim 2, wherein if the pressurization space is enlarged by displacing the separator piston the second hydraulic chamber is caused to become smaller by the same amount.

4. The anesthetic syringe as set forth in claim 1, wherein the syringe comprises a key switch with a touch-sensitive surface that causes the control hole to open at least substantially parallel to the axis of movement of the slide valve when pressed.

5. The anesthetic syringe as set forth in claim 1, wherein a touch-sensitive surface of a key switch is disposed at least partially in a front half of the syringe.

6. The anesthetic syringe as set forth in claim 1, wherein an axis of movement of the slide valve is disposed perpendicular to a longitudinal direction of the syringe.

7. The anesthetic syringe as set forth in claim 1, wherein the slide valve is biased with a biasing force closing the control hole.

8. The anesthetic syringe as set forth in claim 1, comprising an indexer piston that is connected to the first hydraulic chamber.

9. The anesthetic syringe as set forth in claim 8, wherein a foot of the indexer piston projects into the first hydraulic chamber.

10. The anesthetic syringe as set forth in claim 8, wherein the indexer piston is slidably mounted so as to protrude at least partially from the housing of the syringe, with a limit stop for limiting the exit thereof being provided.

11. The anesthetic syringe as set forth in claim 8, wherein the indexer piston is mounted so as to be biased against an exit direction.

12. The anesthetic syringe as set forth in claim 1, wherein, in an inner end position, the feed piston completely lies within a feed cylinder.

13. An anesthetic syringe comprising:
(a) a slide valve comprising a front element;
(b) a feed piston longitudinally slidable within a carpule volume, said fee piston having a feed piston pressure plate;
(c) a first hydraulic chamber connected to said feed piston pressure plate, wherein said feed piston is in use fed forward by a pressure in said first hydraulic chamber;
(d) a second hydraulic chamber behind said first hydraulic chamber and connected to said first hydraulic chamber so as to allow for regulation of flow resistance;
(e) a control hole having an opening between said first hydraulic chamber and said second hydraulic chamber;
(f) a spring connected to said slide valve, said spring biasing said valve to a rest condition wherein the opening of the control hole between said first hydraulic chamber and said second hydraulic chamber is closed; and
(g) a separator piston in a hydraulic system behind the first hydraulic chamber, said separator piston protruding into a pressurization space and into said second hydraulic chamber, said separator piston being slidable so as to reduce the volume of one chamber selected from the group consisting of the pressurization space and the second hydraulic chamber and to enlarge the volume of another chamber selected from the group consisting of the pressurization space and the second hydraulic chamber when being slid;
wherein said slide valve has a slide valve pressure plate connected to said first hydraulic chamber;
wherein said front element protrudes into said first hydraulic chamber in order to allow for haptic feeback of pressure in said first hydraulic chamber; and
wherein said slide valve is capable of closing or progressively opening the opening of the control hole between said first hydraulic chamber and said second hydraulic chamber.

\* \* \* \* \*